United States Patent [19]
Hanawa et al.

[11] Patent Number: 5,972,295
[45] Date of Patent: Oct. 26, 1999

[54] AUTOMATIC ANALYZING APPARATUS

[75] Inventors: Masaaki Hanawa, Hitachinaka; Hiroshi Mitsumaki, Mito; Tadashi Ohishi, Ibaraki-machi; Susumu Kai; Hiroshi Watanabe, both of Hitachinaka, all of Japan

[73] Assignee: Hitachi, Ltd., Tokyo, Japan

[21] Appl. No.: 09/010,182

[22] Filed: Jan. 21, 1998

[30] Foreign Application Priority Data

Jan. 29, 1997 [JP] Japan ................................ 9-015013

[51] Int. Cl.⁶ .................................................. G01N 35/02
[52] U.S. Cl. ................................ 422/65; 422/63; 422/67; 436/43; 436/47; 436/48; 436/50
[58] Field of Search ................................ 422/63, 65, 104, 422/67; 436/43, 47, 48, 174, 50

[56] References Cited

U.S. PATENT DOCUMENTS

| | | | |
|---|---|---|---|
| 4,039,288 | 8/1977 | Moran | 422/65 |
| 4,692,308 | 9/1987 | Riley et al. | 422/65 |
| 5,087,423 | 2/1992 | Ishibashi | 422/67 |
| 5,207,986 | 5/1993 | Kadota et al. | 422/65 |
| 5,209,903 | 5/1993 | Kanamori et al. | 422/65 |
| 5,362,648 | 11/1994 | Koreyasu et al. | 436/48 |
| 5,380,488 | 1/1995 | Wakatake | 422/65 |
| 5,623,415 | 4/1997 | O'Bryan et al. | 364/478 |

FOREIGN PATENT DOCUMENTS

| | | |
|---|---|---|
| 4-65676 | 3/1992 | Japan . |
| 6-207943 | 7/1994 | Japan . |

*Primary Examiner*—Long V. Le
*Attorney, Agent, or Firm*—Fay, Sharpe, Beall, Fagan, Minnich & McKee

[57] ABSTRACT

A sample of a sample rack is sampled at analyzing units in the middle of a transfer line. A standby unit and a rack collecting unit are arranged near an exit of the transfer line. After sample, sampleracks are sorted out to the standby unit or the rack collecting unit at a first switching unit. The racks contained in the standby unit are sorted out to a returning line or the rack collecting unit in a second switching unit corresponding to a judged result of whether or not reexamination is required.

11 Claims, 4 Drawing Sheets

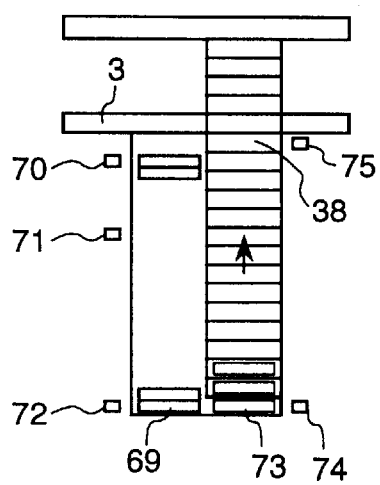 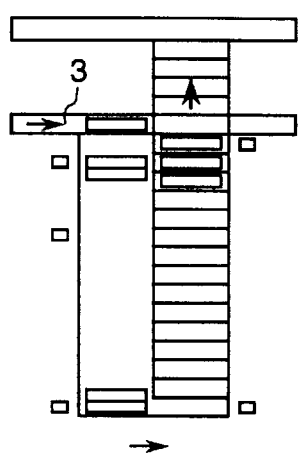 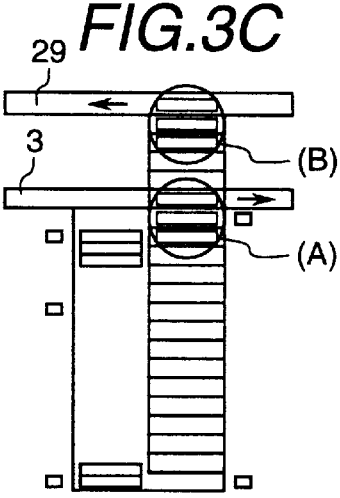
FIG.3A  FIG.3B  FIG.3C
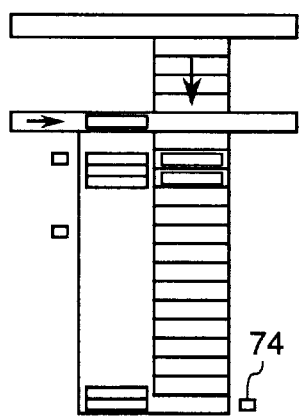 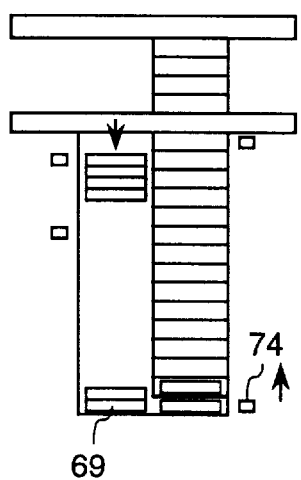 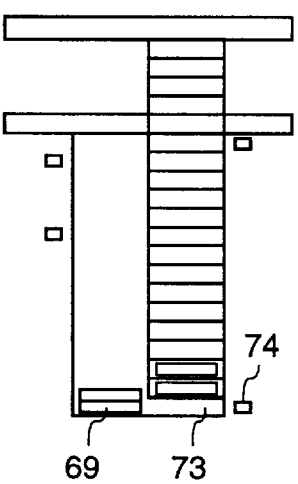
FIG.3D  FIG.3E  FIG.3F
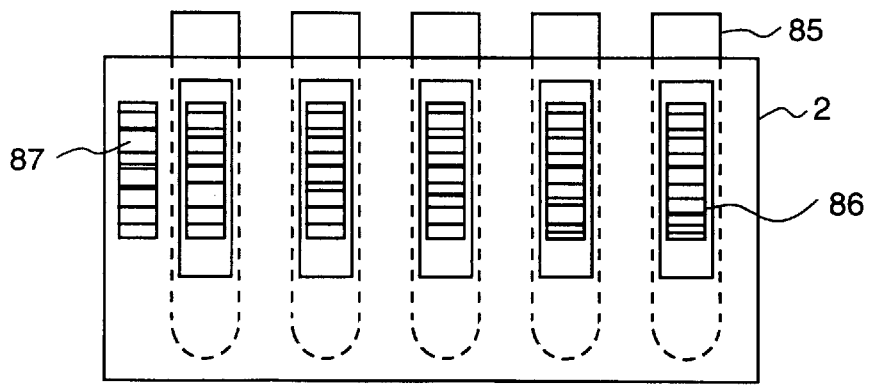
FIG.4

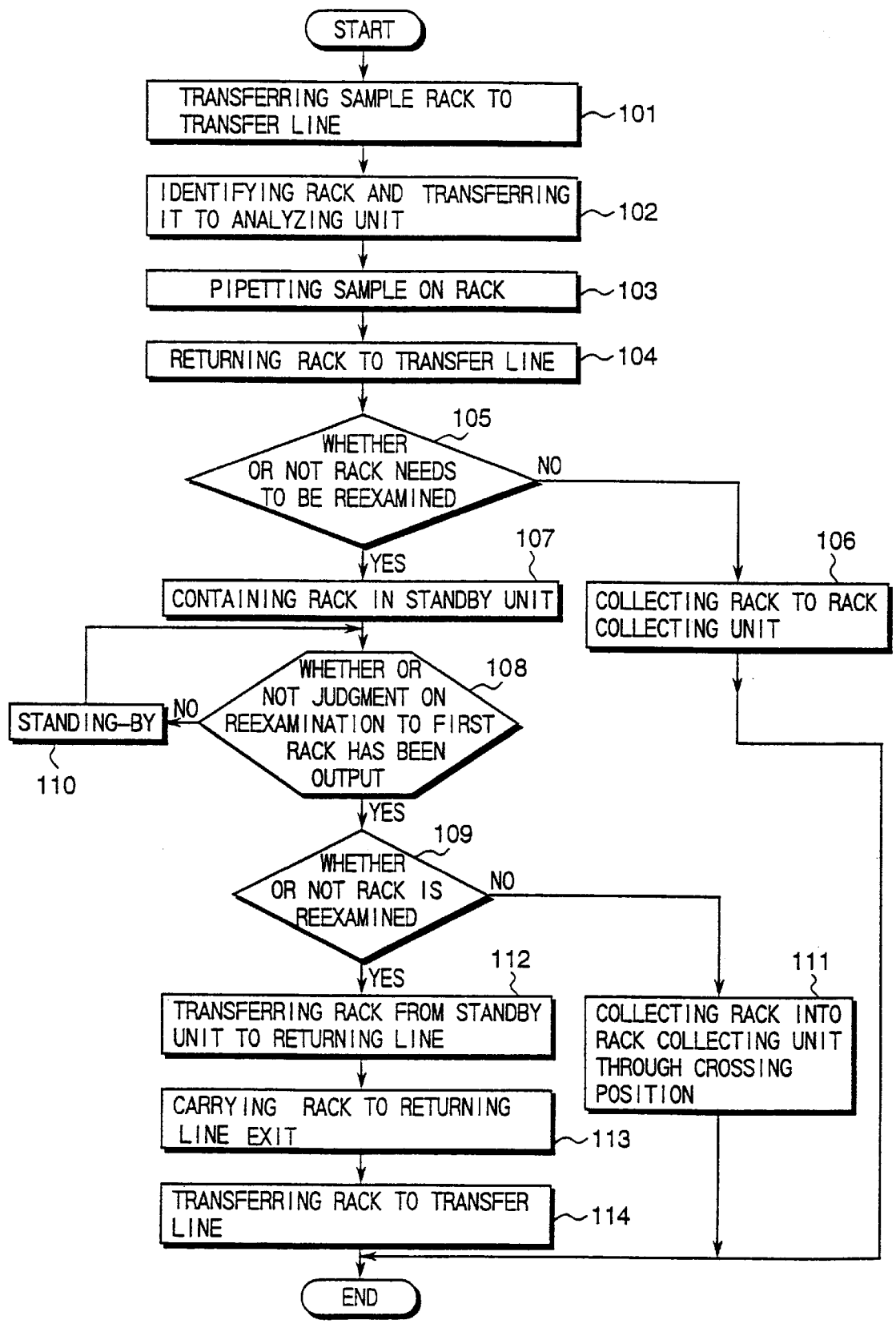

AUTOMATIC ANALYZING APPARATUS

BACKGROUND OF THE INVENTION

The present invention relates to automatic analysis apparatus, and more particularly to an automatic analysis apparatus in which a sample is pipetted from a sample container contained in a sample rack, and the sample is reexamined if necessary.

An automatic analysis apparatus for clinical inspection automatically performs analysis and inspection on analyzing items such as bilirubin, protein, GOT, GPT and the like for a sample such as blood, serum, blood plasma, urine and other body liquids. The automatic analysis apparatus has an analyzing unit for measuring a reaction liquid obtained by reacting a sample with a reagent. As to the methods of supplying the sample to the analyzing unit, there are a method in which a plurality of sample containers are mounted on a turntable and each of the sample containers is positioned at a sample pipetting position by intermittently rotating the turntable, and a method in which a sample rack containing sample containers is positioned at a sample pipetting position of an analyzing unit through a transfer line.

An example of the automatic analysis apparatus in which a sample rack is transferred through a transfer line is disclosed, for example, in Japanese Patent Application Laid-Open No. 4-65676 or in Japanese Patent Application Laid-Open No. 6-207943.

The automatic analysis apparatus disclosed in Japanese Patent Application Laid-Open No. 4-65676 is constructed such that a transfer line for transferring a sample rack in one direction and a transfer line for transferring a sample rack in the other direction are arranged in parallel, a sample rack supplied from a rack supply unit is transferred by the transfer line, a sample on the sample rack is pipetted to the analyzing unit at a sample sucking position provided on the transfer line, and the sample rack is placed in a rack collecting unit through the returning line after sampling. Further, in some midpoint of the returning line there is provided a rack standby space for keeping a reference sample for accuracy management on standby. The reference sample rack is periodically transmitted to the transfer line, and the sample rack is returned again to the rack standby by space through the returning line after sampling.

On the other hand, the analysis apparatus disclosed in Japanese Patent Application Laid-Open No. 6-207943 is constructed such that a standby unit for a sample rack is provided near a rack supply unit, a sample rack supplied from the rack supply unit is transferred by a transfer line, a sample is pipetted from the sample rack to the analyzing unit on the transfer line, and the sample rack is transferred to an exit of the returning line after sampling through the returning line. Further, sample racks having a probability of being reexamined are transferred from an exit of the returning line to the standby unit using a robot-hand, and sample racks not having a probability of being reexamined are transferred from the exit of the returning line to a rack collecting unit using the robot-hand. When an instruction of reexamination is made to a sample rack on standby in the standby unit, the corresponding sample rack is transferred to an entrance of a transfer line and pipetting of a sample to be reexamined is performed on the transfer line.

Both of the analysis apparatuses of the prior art disclosed in Japanese Patent Application Laid-Open No. 4-65676 and in Japanese Patent Application Laid-Open No. 6-207943 are constructed such that all the sample racks transferred by the transfer line are transferred through the returning line, and then contained in the standby unit or in the collecting unit.

In the practical work of sampling inspections, the in number of sample racks for general samples which are judged to need to be reexamined is less than the number of sample racks which are judged not to need to be reexamined; therefore, it can be said that a large number of sample racks which may be judged not to need be reexamined are transferred through the returning line.

When the above-mentioned prior art is applied to an automatic analysis apparatus so as to have a reexamination function for general samples, there occurs a problem in that a large number of sample racks are gathered at the exit of the returning line and a complex handling mechanism for solving the problem is required.

SUMMARY OF THE INVENTION

An object of the present invention is to provide an automatic analysis apparatus which can reduce the frequency of transferring the sample racks through the returning line when the automatic analysis apparatus is added with a reexamination function for ordinary samples.

Another object of the present invention is to provide an automatic analysis apparatus in which the mechanism for handling the sample racks at the exit side of the returning line can be simplified and the mechanism for handling the sample racks at the exit side of the transfer line can be not so complicated.

The present invention is applied to an automatic analyzing apparatus comprising a rack supply unit capable of containing sample racks, an analyzing unit for testing an instructed analysis item to a sample sampled from a sample container contained in the sample rack, a transfer line for transferring a sample rack supplied from the rack supply unit to a position corresponding to the analyzing unit and transferring the sample rack after being sampled to an exit of the transfer line, a standby unit for keeping sample racks having a probability of being reexamined stand-by, a returning line for returning the sample rack after being sampled to an entrance side of the transfer line, and a rack collecting unit for containing sample racks not required to be reexamined.

One concept of the present invention is characterized by standby unit being arranged so as to be interposed between the analyzing unit and the collecting unit, and by a directing apparatus for selectively directing a sample rack after sampling to either the analyzing unit or the collecting unit.

Another concept of the present invention is characterized in that a transfer passage from the exit of the transfer line to the rack collecting unit and a passage for moving the sample rack standing-by at the standby unit to an entrance of the returning line are arranged so as to cross to each other.

BRIEF DESCRIPTION OF THE DRAWINGS

FIG. 3A to FIG. 3F are views showing movement of sample racks inside the standby unit.

FIG. 4 is a view showing an embodiment of a sample rack.

FIG. 5 is a flow diagram showing a transferring process of a sample rack.

DESCRIPTION OF THE PREFERRED EMBODIMENTS

Figure 1:
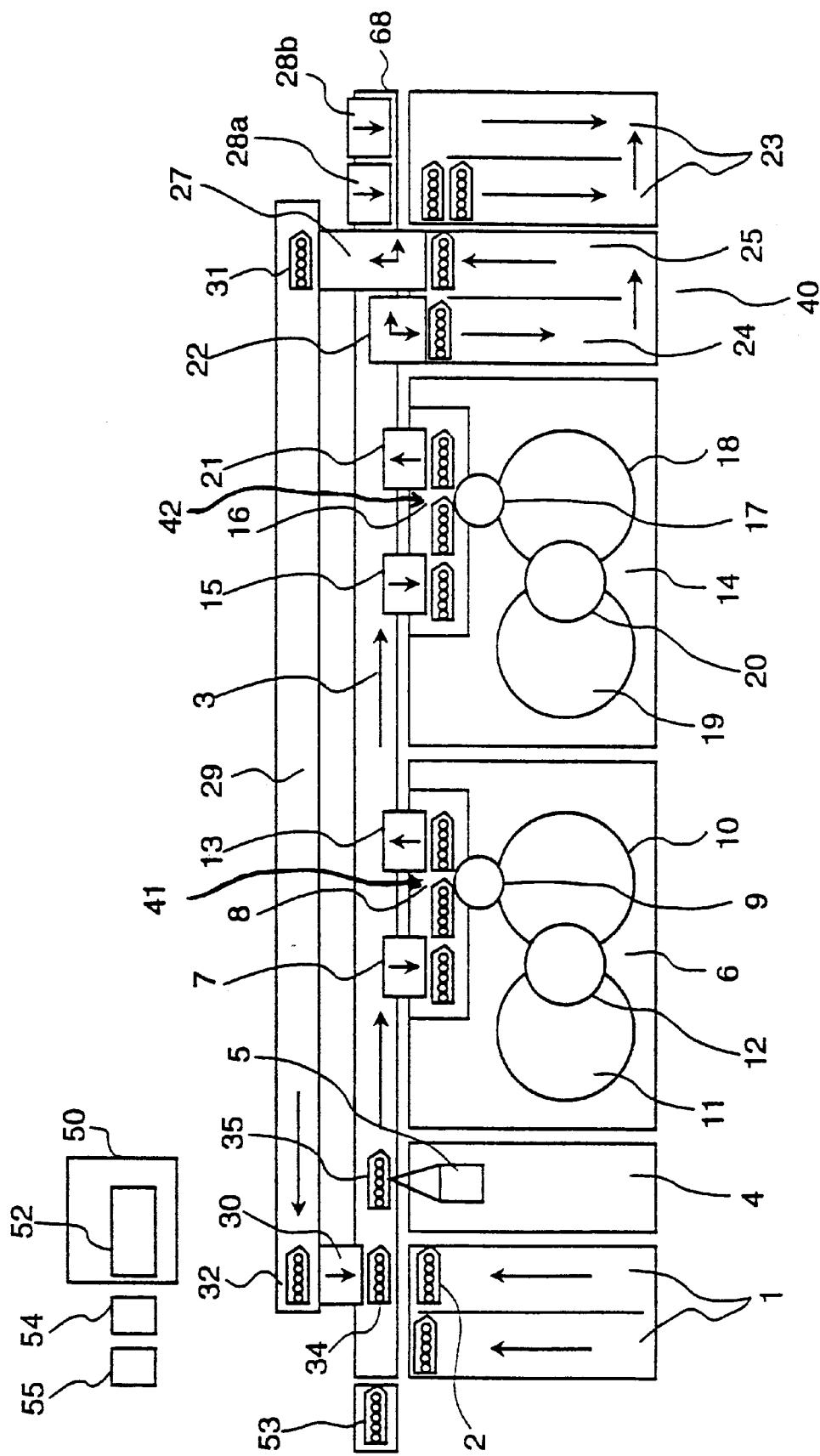
FIG. 1 is a schematic view showing the overall construction of an embodiment of an automatic analysis apparatus in accordance with the present invention.

In a preferable embodiment of the present invention, five sample containers containing samples to be analyzed for examination are contained in each of a plurality of sample racks. A transfer line for transferring sample racks to be analyzed for examination and a returning line for transferring sample racks to be reexamined, are arranged adjacent to and parallel to each other. A plurality of analyzing units are arranged along the transfer line, and at least one of the analyzing units can perform random-access processing of various kinds of multi-item analysis.

Operations of the analyzing unit and respective mechanisms in the automatic analyzing apparatus are controlled by a control unit composed of a microcomputer according to a predetermined operation program. Before or at the time when a sample rack carried by the transfer line arrives at an exit of the transfer line, it is identified whether the sample rack carried is a sample rack which needs not to be reexamined or a general sample rack which may need to be reexamined. Then, at a distributing position of the exit of the transfer line which also serves as an entrance of a standby unit, the sample rack is selectively directed based on the identified result using a directing apparatus. A sample rack which is pre-registered as not needing to be reexamined is moved to an entrance of a rack collecting unit passed across a crossing position beside an exit of the standby unit and then contained in the rack collecting unit.

An ordinary sample rack which may need to be reexamined is moved into the standby unit from the sorting out position also serving as the entrance of the standby unit so as to be kept standing-by inside the standby unit until it is judged according to an analyzing examination of the analyzing unit whether or not reexamination is required. The sorting out position also serving as the exit of the transfer line is arranged in series with the crossing position and the entrance of the collecting unit and provided on an extending line of the transfer line.

The ordinary sample rack having a first examination result is directed so as to be moved from the exit of the standby unit to the entrance of the returning line or the entrance of the rack collecting unit through the crossing position. That is, the sample rack judged to need to be reexamined is carried to the entrance of the returning line through the crossing position, and the sample rack judged to need not to be reexamined is carried to the entrance of the rack collecting unit to be sorted in the rack collecting unit. The crossing position is a place where a passage for moving the sample rack from the exit of the transfer line to the entrance of the rack collecting unit and a passage for moving the sample rack from the exit of the standby unit to the entrance of the returning line cross each other. The crossing position is a place where a path for the sample rack judged to need to be reexamined and a path for the sample rack judged to need not to be reexamined cross each other. Therefore, movement of a sample rack in one direction is performed while movement of a sample rack in the other direction crossing with the one direction is being stopped.

The sample rack entered in the standby unit is moved along a U-shaped path. The standby unit has a receiving area for a sample rack near the entrance of the standby unit and a sending-out area for a sample rack near the exit, and the sample rack is moved between both areas during a standing-by time when the sample rack is kept waiting for judgment on whether or not reexamination is needed. In the sending-out area of the standby unit, there is provided a conveyer belt which can move a lot of sample racks at a time, and each of the sample racks is positioned at the exit of the standby unit using the conveyer belt. Further, the conveyer belt is extended up to the entrance of the returning line outside the standby unit, and serves as a transfer apparatus for transferring the sample rack from the exit of the standby unit to the entrance of the returning line.

The sample rack is mounted on the conveyer belt in such a manner that the longitudinal direction of the sample rack crosses the traveling direction of the conveyer belt. In the conveyer belt, there are formed a lot of partition members in parallel to one another, and the sample rack is contained in a gap between the partition members. Thereby, the sample rack is prevented from falling down during the conveyer movement. When the conveyer belt is stopped, a space formed by two of the partition members becomes a passage for moving the sample rack from the exit of the transfer line to the rack collecting unit. Therefore, the partition members are positioned not to interrupt the sample rack from passing through.

An embodiment of the present invention will be described below, referring to FIG. 1 to FIG. 5. Referring to FIG. 1, a tray having many aligned sample racks 2 is loaded in a rack supply unit 1 having two columns of set-spaces. The sample racks 2 in the rack supply unit are pushed into the exit 34 of the rack supply unit one-by-one using a well-known rack pushing mechanism. The rack 2 pushed out to the exit 34 is moved up to the entrance 35 of the transfer line by a hook movable horizontally.

As shown in FIG. 4, each of the sample racks 2 is a rectangular-block-shaped supporting body, and five sample containers 85 are held and aligned in a row along the longitudinal direction of the rack. The sample rack 2 has a bar-code label 87 indicating a rack kind and a rack number. Each of the sample containers 85 also has a bar-code label 86, indicating a container identification number or a sample reception number.

Figure 2:
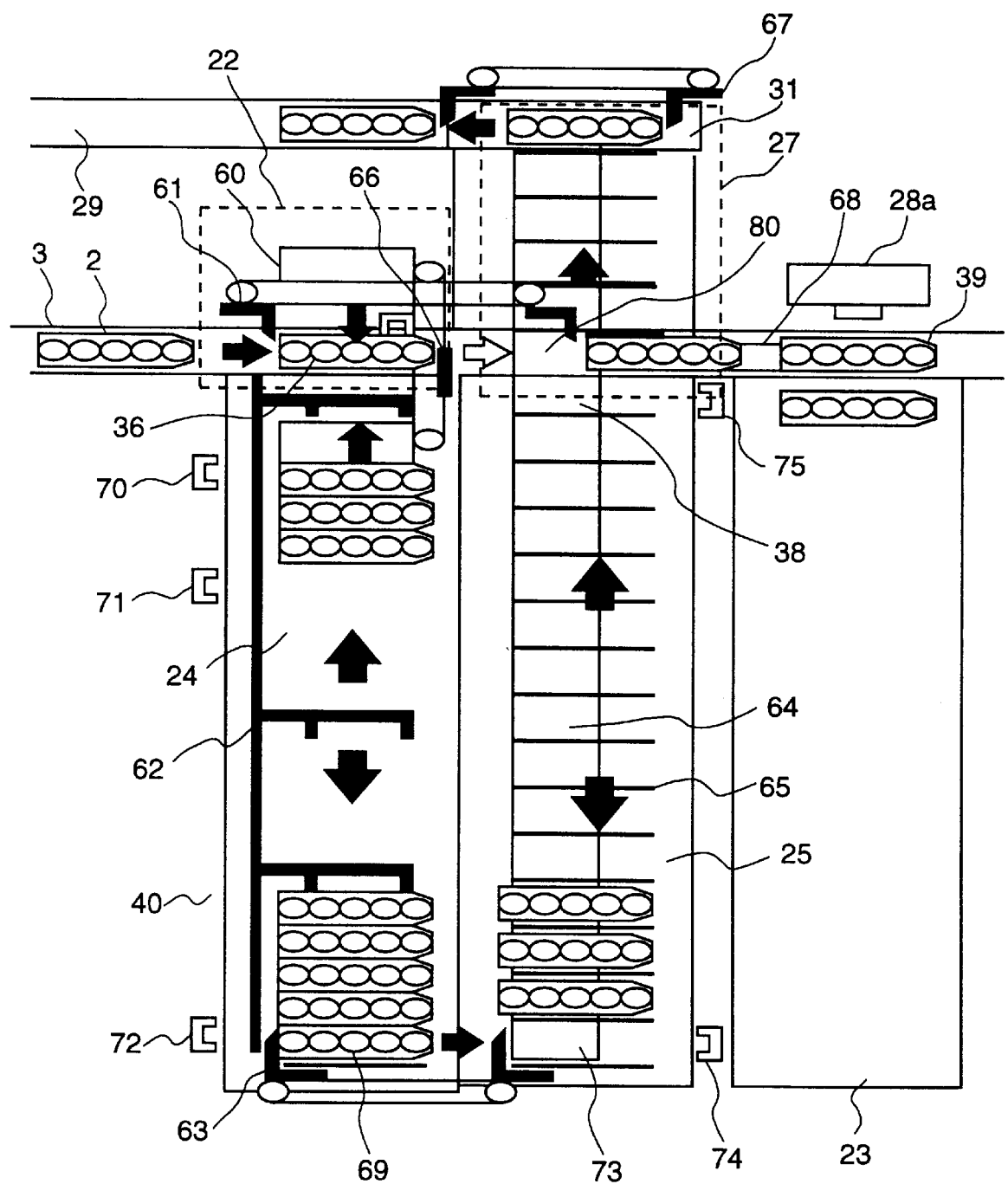
FIG. 2 is a view explaining operation near the standby unit of the embodiment of FIG. 1.

The transfers line 3 in FIG. 1 is composed of a belt line rotating upward and downward, and the transfer operation is controlled so that the sample rack is stopped at predetermined positions. The transfer line 3 can carry the sample rack from the entrance 35 of the transfer line to the exit 36 of the transfer line (FIG. 2). The rack identifying unit 4 in FIG. 1 has a bar-code reader 5 as an identifying apparatus for identifying a destination of the sample rack coming to the entrance of the transfer line. The identifying apparatus of this kind may be provided at the analyzing units 6, 14 or the exit of the transfer line in addition to being at the rack identifying unit 4. The content of the bar-code label 87 of the rack and the content of bar-code label 86 of each of the sample containers read by the bar-code reader 5 are transmitted to a control unit 50, and the rack kind, the kind of analysis item instructed to each of the sample containers and so on are compared with analysis information pre-instructed from an operating unit 55 corresponding to the sample reception numbers. Based on the compared results, the destination of the sample rack 2 is determined by the control unit 50 and stored in a memory 52 to be used for processing of the sample rack to be performed later.

The entrance 35 of the transfer line is a starting point of transferring of the transfer line 3, and the sample rack 2 identified by the rack identifying unit 4 is transferred up to a position of a rack in-take mechanism 7 or 15 corresponding to the analyzing unit 6 or 14, and stopped once to be taken in a sampling area 8 or 16 of the analyzing unit 6 or 14 by the rack in-take mechanism 7 or 15.

The upstream of the transfer line 3, there is provided an emergency sample inputting unit 53 to which a sample rack 2 for emergency examination can be set, and the sample rack placed here is carried to the entrance 35 of the transfer line by giving priority over the ordinary sample racks for general examination using a rack carrying hook, to proceed with the analysis examination by the analyzing unit.

The analyzing unit 6 or 14 arranged along the transfer line 3 comprises a sampling area 8 or 16 for receiving a sample rack from the transfer line 3 and returning the sample rack after pipetting processing to the transfer line again, a reaction disk 10 or 18 for forming a reaction line by a row of reaction containers and rotating the row of the reaction containers so as to progress reaction of samples and reagents corresponding to various kinds of analysis items in the respective reaction bottles, and a reagent disk 11 or 19 for positioning reagents corresponding to various kinds of analysis items to a reagent sucking position. Further, the analyzing unit 6 or 14 comprises a multi-wavelength photometer for measuring a reaction solution of each of the samples formed in the reaction container, a sample pipetting mechanism 9 or 17 for pipetting a sample in the sample container in the sampling area 8 or 16 to the reaction container on the reaction disk 10 or 18, and a reagent pipetting mechanism 12 or 20 for pipetting a reagent corresponding to an analysis item from a reagent bottle on the reagent disk 11 or 19 to a reaction container on the reaction disk 10 or 18.

The sample rack 2 holding a sample to which the first analyzing unit 6 instructs an item to be analyzed is moved from the transfer line 3 to the sampling area 8 by the rack intake mechanism 7. The transferred sample rack 2 is moved inside the sampling area 8 from the intake position to a sample pipetting position 41, and a pipetting nozzle of a sample pipetting mechanism 9 is inserted into a necessary sample container to perform pipetting to a reaction bottle. When two or more items of analysis are instructed to the same sample container or when the same analysis item is instructed to the other sample container on the same sample rack, the sample pipetting operation is successively repeated.

The sample rack 2 of which pipetting of samples in regard to all the analysis items instructed is completed is moved to a position corresponding to a rack ejecting mechanism 13, and mounted on the transfer line 3 by the rack ejecting mechanism 13. On the other hand, the sample pipetted to the reaction container on the reaction disk 10 is reacted with a reagent pipetted by a reagent pipetting mechanism 12, and after a predetermined time the reaction solution is measured by the multi-wavelength photometer, and the data corresponding to each analysis items is output to the control unit 50. The control unit 50 compares the analysis data with predetermined judging references. If the measured result is judged to be inappropriate, the control unit 50 stores the fact that the sample needs to be reexamined, in association with the sample rack number and the sample container number, into a predetermined memory area of the memory unit 52 to control the operation of a direction apparatus, to be described later, at an appropriate timing.

To the sample rack moved onto the transfer line 3 by the rack ejecting mechanism 13, the control unit 50 judges whether or not the sample rack mounts a sample required to be analyzed on an analysis item set to the second analyzing unit 14. If there is a sample required to be analyzed on the sample rack 2, the sample rack is carried up to the position corresponding to the rack intake mechanism 15 by the transfer line 3. The sample rack stopped on the transfer line 3 is moved into a sampling area 16 by the rack in-take mechanism 15, and then at the sample pipetting position, 42 the sample is pipetted to a reaction container on the reaction disk 18. The sample rack 2 of which pipetting of all necessary samples from the sample containers is completed is moved onto the transfer line 3 by the rack ejecting mechanism 21. Then the sample rack 2 is transferred up to the exit of the transfer line.

Each sample rack having sample containers containing a control sample, a reference sample, a cleaning solution and the like has a different color from the sample rack for ordinary samples in the outward appearance. However, these sample racks are pre-registered in a sample kind table in the memory 52 of the control unit 50 as racks not required to be reexamined. When a sample rack is identified as a general sample rack by the bar-code reader 5, the control unit 50 operates the rack pushing mechanism 60 (FIG. 2) of the directing apparatus so that the sample rack is taken into the standby unit 40 at the sorting out position, which also serves as the exit of the transfer line.

The directing apparatus for selectively directing out sample racks in the direction instructed by the control unit 50 comprises a first switching unit 22 and a second switching unit 27. The first switching unit 22 directs a sample rack to the standby unit 40 or to the rack collecting unit 23 in accordance with rack identifying information by the bar-code reader 5. The second switching unit 27 directs a sample rack to the returning line 29 or to the rack collecting unit 23 in accordance with a judged result on necessity of reexamination by the control unit 50 based on examination results of the analyzing units 6 and 14. All the sample racks except for the racks pre-registered as the racks not required to be reexamined are once contained in the standby unit 40 after sample pipetting in the analyzing units.

The sample racks contained in the standby unit 40 are kept waiting until the examination results of the analyzing units 6, 14 are output to the control unit 50 while being moved between the receiving area 24 and the sending-out area 25. A sample rack judged to need not to be reexamined is moved from the exit of the transfer line 3 or from the exit of the standby unit 40 to the entrance of the rack collecting unit on a collecting line 68, and puts it into the rack collecting unit 23 by the rack pushing mechanism 28a or 28b.

The returning line 29 is composed of a belt line rotated upward and downward so as to be extended between the entrance 31 of the returning line and the exit 32 of the returning line. A sample rack 2 that is moved from the standby unit 40 to the entrance 31 of the returning line as being judged to need to be reexamined, is transferred up to the exit 32 in the end terminal of the returning line by the returning line 29 without interrupting the transfer of the other sample racks. Then, the sample rack is moved from the exit 32 of the returning line to the exit 34 of the rack supply unit by a rack moving mechanism 30, and after that the sample rack is moved to the entrance 35 of the transfer line to be conducted to the analyzing units 6, 14 again through the transfer line 3. The first analysis data and the reexamination analysis data are displayed on a display unit 54. It is programmed that the sample rack to be reexamined is transferred to the transfer line 3 in giving priority over the racks supplied from the rack supply unit 1. By doing so, the final analyzed result in regard to a sample of which analysis is started first can be obtained as early as possible.

The standby unit 40 of FIG. 1 is arranged so as to be interposed between the analyzing unit 14 and the rack collecting unit 23, and thereby a sample rack judged to need not to be reexamined can be quickly entered into the rack collecting unit 23 without interrupting treatment of the other sample racks. Since sample racks having been sample-pipetted are concentratively sorted out near the exit of the transfer line 3, the rack treating mechanism near the exit of the returning line 29 can be simplified.

FIG. 2 is a plan view showing the detailed construction near the standby unit of the automatic analyzing apparatus of FIG. 1. In FIG. 2, the first switching unit 22 and the second switching unit 27 are shown by broken lines. The first switching unit 22 comprises a rack pushing mechanism 60 for reciprocally moving a rack contact member in a direction crossing at a right angle with the longitudinal direction of the sample rack 2, a rack transfer mechanism 61 for moving a hook for pushing a rear end portion of a sample rack 2 by the rotating belt, and a rack stopper 66 for moving a member for stopping movement of the sample rack by the rotating belt. The second switching unit 27 comprises an endless belt 64 rotated upward and downward, a rack transfer mechanism 61 having a hook for mounting a sample rack 2 on the belt of the collecting line 68 by pushing the rear end portion of the sample rack 2 positioned at a crossing position 80, and a rack transfer mechanism 67 for moving a hook for pushing the rear end portion of the sample rack 2 coming to the entrance 31 of the returning line 29 by the rotating belt.

The exit 36 of the transfer line also serves as the sorting out position of the sample racks and the entrance of the standby unit 40. The sample rack 2 ejected from the analyzing unit 6 or 14 and carried by the transfer line 3 is selectively directed at the exit 36 of the transfer line depending on whether the rack needs not to be reexamined. When a sample rack determined to need not to be reexamined arrives at the exit 36 of the transfer line, the rack stopper 66 is in an off-state from the passage and the sample rack is pushed on the rear end portion by the rack transfer mechanism 61 to be transferred to the collecting line 68 by passing through the crossing position 80 and stopped at the entrance 39 of the collecting unit. Then the sample rack is entered into the rack collecting unit 23 by being pushed in the direction crossing at a right angle in the longitudinal direction of the sample rack 2 by the rack pushing mechanism 28a or 28b.

On the other hand, when a sample rack 2 having a probability to be reexamined arrives at the exit 36 of the transfer line, the rack stopper 66 is moved to a position to close the passage to stop the sample rack from proceeding, and the sample rack is pushed into the standby unit 40 by operation of the rack pushing mechanism 60. In the standby unit 40, there are provided rack sensors 70, 71, 72, 74 and 75 composed of reflection type photo-sensors at several positions. Two kinds of mechanisms for carrying the sample rack 2 in the standby unit 40 are employed. That is, the rack transfer mechanism 62 having a movable arm serves in the receiving area 24 from the entrance of the standby unit to a delivery position 69, and the belt 64 serves in the sending-out area 25 from the receiving position of the sample rack 2 to the exit 38 of the standby unit.

Entry of the sample rack 2 into the standby unit 40 by the rack pushing mechanism 60 is detected by a rack sensor 70. When the sample racks directed from the exit 36 of the transfer line or the entrance of the standby unit are successively pushed into the standby unit 40 and the number of the sample racks pushed into the standby unit 40 near the entrance side reaches a preset number, the first sample rack is detected by the second rack sensor 71. When the control unit 50 receives the detecting signal of the rack sensor 71 or when a time period from receiving of a sample rack to receiving of the following sample rack is longer than a preset value, a plurality of sample racks 2 staying between the rack sensor 70 and the rack sensor 71 are moved to the delivery position 69 by the rack transfer mechanism 62 corresponding to an instruction of the control unit 50. Arrival of the first sample rack at the delivery position 69 is detected by the rack sensor 72 and the information is transmitted to the control unit 50.

In the embodiment of FIG. 2, the number of sample racks to be carried at once is determined based on the distance between the rack sensor 70 and the rack sensor 71. Instead of this method, it is possible to employ a method where the number of the sample racks 2 detected by the rack sensor 70 is counted, and the sample racks are transferred to the delivery position 69 by the rack transfer mechanism 62 when the number reaches a preset value. Otherwise, it is possible that every time the sample rack is contained in the standby unit 40 from the entrance of the standby unit, the sample rack is transferred to the delivery position 69 one-by-one.

The belt 64 installed in the sending-out area 25 of the standby unit 40 has a function to transport the sample rack 2 received at the receiving position 73 to the exit 38 of the standby unit, a function to move the sample rack placed in the exit 38 of the standby unit, and a function to move the sample rack in the exit 38 of the standby unit to the entrance 31 of the returning line. The belt 64 has plural partition members 65 arranged such that the distance between them is slightly larger than the width of the sample rack. Therefore, when the sample rack is contained in the space between adjacent partition members adjacent, the sample rack can be prevented from falling down. Two of the partition members 65 facing the crossing position 80 serve as side walls of the passage of the sample rack passing through the crossing position 80 toward the entrance 39 of the collecting unit.

The sample rack 2 moved to the delivery position 69 by the rack transfer mechanism 62 is transferred from the transfer position 69 to the receiving position 73 by the rack transfer mechanism 63 having the hook contact to the rear end portion of the sample rack after the control unit 50 confirms information by the rack sensor 72 that there exists a sample rack on the delivery position 69, and information by the rack sensor 74 in the side of the receiving position 73 that there does not exist a sample rack on the receiving position 73. As the control unit 50 receives the information from the rack sensor 74 that a sample rack is detected, the control unit 50 drives the belt 64 to move the belt by a distance of one rack. This operation is repeated until a certain number of the sample racks are positioned in the delivery position 69 by the rack transfer mechanism 62.

The rack sensor 74 has a counter function. In a case where the rack sensor 7.4 is a reflection type photo-sensor as in this embodiment, by the rack sensor 74 transmitting a signal changing from dark to bright or a signal changing from bright to dark to the control unit 50, the number of sample racks contained in the sending-out area is stored in the memory 52 and managed for later processing of the sample racks.

During working to transfer a sample rack 2 onto the belt 64, a sample rack 2 arriving at the exit 36 of the transfer line from the transfer line 3 is contained into the receiving area 24 of the standby unit 40 by the rack pushing mechanism 60 at any time. When the number of sample racks in the standby unit 40 is reaches a predetermined number by containing newly coming sample racks 2 into the standby unit 40 by the rack transfer mechanism 62 even if a plurality of sample racks 2 transferred to the side of the rack sensor 72 are not completed to be moved from the receiving area 24 to the sending-out area 25, the rack transfer arm of the rack transfer mechanism 62 is returned to the entrance side of the standby unit and the plurality of sample racks newly contained are moved so as to be arranged following the row of the sample racks before being moved to the sending-out area 25. By doing so, stagnation of the sample racks near the entrance of the standby unit can be prevented.

The sample racks 2 contained in the standby unit 40 are ejected from the exit 38 of the standby unit in order of being transferred by the transfer line 3. When the control unit 50 outputs a judgment on whether or not reexamination is needed for the first sample rack in the sending-out area 25 based on the examination results of the analyzing units 6, 14, the transfer belt 64 is driven so that the first sample rack 2 is positioned at the exit 38 of the standby unit. Arrival of the first sample rack at the exit 38 of the standby unit is confirmed by the rack sensor 75.

When the first sample rack is judged to need not to be reexamined, the belt 64 is moved by a distance of one rack and the sample rack having existed at the exit 38 of the standby unit is transferred to the crossing position 80. The sample rack is transferred to the collecting line 68 by the rack transfer mechanism 61 to be contained in the rack collecting unit 23 through the entrance 39 of the rack collecting unit by using the rack pushing mechanism 28a or 28b.

On the other hand, when the first sample rack is judged to need to be reexamined, the belt 64 is moved so that the sample rack existing at the exit of the standby unit is transferred to the entrance 31 of the returning line. The sample rack arriving at the entrance 31 of the returning line is moved onto the returning line 29 by the rack transfer mechanism 67 to be transferred to the exit 32 of the returning line by transferring operation of the returning line 29 at once. Every time a first sample rack in the sending-out area 25 is positioned at a position of the exit 38 of the standby unit, the above-mentioned treatment is made depending on the necessity of reexamination, so that the sample racks are sorted into sample racks to be sent from the crossing position 80 toward the rack collection unit 23 and into sample racks to be sent straight on the crossing position 80 toward the entrance 31 of the returning line.

The maximum staying time of a sample rack in the standby unit 40 being kept waiting in the standby unit 40 is approximately twice as long as the time period of analyzing a sample on an analysis item requiring the maximum reaction time in the analyzing units 6, 14. The maximum number of the sample racks to be kept waiting in the standby unit 40 is determined by the maximum reaction time. For example, in a case where the number of sample containers contained in a sample rack is 5, the maximum reaction time is 10 minutes, the sample pipetting interval is 4.5 seconds and sampling is performed from each of the sample containers item by item, it is sufficient that the standby unit can contain 27 sample racks. Since the number of sample racks is 54 when the maximum reaction time is twice the above in taking a margin into consideration, it is sufficient that the containing space of sample racks in the standby unit 40 is above 27 and below 54 on the rack number base.

FIG. 3A to FIG. 3F are views showing the moving operation of the sample racks 2 inside the standby unit 40. In a state of containing sample racks as shown in FIG. 3A, it is assumed that whether or not reexamination is needed for the first sample rack in a row of the racks has been judged. Letting the maximum containable number of racks from the receiving position 73 to the exit 38 of the standby unit be n, in the case of FIG. 3, n is 15. Letting the number of racks actually placed in the sending-out area 25 be nx (in the case of FIG. 3, the number nx is 3), and letting a moving distance corresponding to one rack be one pitch, the distance for moving the first sample rack to the exit 38 of the standby unit is (n–nx) pitches. A state after moving is shown in FIG. 3B.

In a case where the judged result is that reexamination of the first sample rack is not needed, the belt 64 is moved forward by one pitch, and the sample rack is collected to the rack collecting unit 23 through the crossing position 80. On the contrary, in a case where the judged result is that reexamination of the first sample rack in the state of FIG. 3B is needed, the belt 64 is moved forward by a required number of pitches (in the case of FIG. 3, six pitches), and only the first sample rack is transferred to the entrance 31 of the returning line. That is, the belt 64 is moved forward from the state (A) of FIG. 3C to the state (B). Then, the belt 64 is moved backward by the above-mentioned required number of pitches to obtain the state of FIG. 3D. On the other hand, in the case where the judged result is that reexamination is not needed, the belt 64 is moved backward by one pitch to obtain the state of FIG. 3D.

In the next step, the belt 64 is moved backward by (n–nx) pitches to get the state of FIG. 3E. In the state of FIG. 3E, the last sample rack of the rack row in the sending-out area 25 is detected by the rack sensor 74. When the control unit 50 recognizes this detecting signal, the control unit 50 reduces the count number of the contained racks by one and the result is stored in the memory 52. Then, the belt 64 is moved forward by one pitch to prepare for receiving a sample rack from the delivery position 69 to the receiving position 73. This state is shown in FIG. 3F.

After the state of FIG. 3F, when a sample rack exists in the delivery position 69, the sample rack is moved to the receiving position 73 and the operation starting from the state of FIG. 3A is repeated. On the other hand, when a sample rack does not exist in the delivery position 69, the belt 64 keeps the state of FIG. 3F until judgment on whether or not reexamination is needed for the first sample rack in the sending-out area 25 is output. In this case, if judgment on whether or not reexamination is needed for the first sample rack has been output, transferring of the rack row by the belt 64 is immediately started.

FIG. 5 is a flow diagram showing the transferring process of the sample racks in the automatic analyzing apparatus of FIG. 1. In Step 101, a sample rack is moved from the rack supply unit 1 to the entrance 35 of the transfer line as the transferring starting point on the transfer line 3. By the bar-code reader 5 of the rack identification apparatus, the sample rack on the entrance 35 of the transfer line is identified as to whether or not the sample rack needs to be reexamined, as to sample information of the sample containers arranged on the sample rack. The identified information is transmitted to the control unit 50 to be stored in the memory 52 (Step 102). Further, in Step 102, transferring by the transfer line 3 is started, and the sample rack is moved to a position corresponding to the analyzing unit 6 or 14 for analyzing analysis items instructed for the samples on the sample rack.

In Step 103, the sample rack is shifted from the transfer line to the sampling area 8 or 16, and the samples for the analysis items instructed for the samples on the sample rack are pipetted into reaction containers on the reaction disk 10 or 18. The sample rack is then returned onto the transfer line 3 again in Step 104.

Based on the stored identification information, the control unit 50 judges whether the transferred sample rack may needs to be reexamined (Step 105). If the sample rack does not need to be reexamined, the processing proceeds to Step 106. The sample rack after being transferred is collected in the rack collecting unit 23 and the process of the sample rack is completed. The sample rack which has been judged in Step 105 to possibly need to be reexamined is moved to Step 107 and contained in the standby unit 40 by the rack directing apparatus.

Analysis results corresponding to the samples by the analyzing unit 6 or 14 are output while the sample rack is moved in the standby unit 40, and based on the analysis results the control unit 50 judges whether or not the sample to be reexamined is on the sample rack. In Step 108, it is checked whether or not the judgment on necessity of reexamination to the first sample rack in the rack row arranged in the standby unit 40 has been output. If the judgment has been output, it is judged in Step 109 whether or not the judgment is that the sample is to be reexamined. If the judgment has not been output yet, the processing proceeds to Step 110 to keep the first sample rack waiting in the standby unit 40 until the judgment on necessity of reexamination is output.

The sample rack which has been judged in Step 109 to need not to be reexamined is collected into the rack collecting unit 23 through the crossing position 80 according to Step 111 and the processing is completed. On the other hand, the sample rack which has been judged in Step 109 to need to be reexamined is moved from the standby unit 40 to the entrance of the returning line according to Step 112. In Step 113, the sample rack is carried to the exit 32 of the returning line. The sample rack is transferred to the entrance 35 of the transfer line and identified. Then, the sample rack is transferred by the transfer line 3 to the analyzing unit 6 or 14 to be reexamined.

Since in the above-mentioned embodiment the standby unit 40 is arranged adjacent to and between the analyzing unit 14 and the rack collecting unit 23, a sample rack not needing to be reexamined can be collected to the rack collecting unit without passing through the returning line. By doing so, the majority of racks not needing ne to be reexamined can be collected immediately after coming out from the transfer line or from the standby unit. Therefore, the number of racks transferred to the returning line can be substantially reduced. The sample racks contained in the standby unit 40 are sent out from the standby unit to the instructed destinations from the head of the rack row on standing-by in arranged order. Since only the sample racks needing to be reexamined are transferred in the returning line, stagnation of sample racks near the exit of the returning line can be eliminated.

Further, by providing the crossing region of the passage of the rack to be collected and the passage of the rack to be reexamined near the exit of the standby unit, it is possible to prevent the transfer passages of the sample racks having different destinations from becoming complex, long and large. Furthermore, since the mechanism for transferring racks can have plural functions, the mechanism can be simplified.

In addition, in the above-mentioned embodiment, the sample racks completed to be transferred by the transfer line after sampling are immediately sorted out near the exit of the transfer line 3 by the directing apparatus. The sample rack has been judged based on the rack identification information whether or not the sample rack needs to be reexamined before the sample rack arrives at the sorting out position, and the destination of the sample rack is determined based on the judgment of whether or not the sample rack needs to be reexamined. The directing apparatus comprises the first switching unit for sorting out the sample racks arriving at the exit of the transfer line to be contained into the standby unit 40 or to be collected into the rack collecting unit 23; and the second switching unit for directing the sample racks waiting in the standby unit 40 to either the returning line 29 or the rack collecting unit 23. However, since the directing apparatus is constructed such that one rack transferring mechanism is used in both switching units, the directing mechanism can be simplified.

According to the present invention, the frequency of transferring sample racks by the returning line can be reduced, and, accordingly stagnation of the sample racks in the exit side of the returning line can be eliminated.

What is claimed is:

1. An automatic analyzing apparatus, comprising:

a rack supply unit capable of containing sample racks;

an analyzing unit for testing an analysis item of a sample sampled from a sample container contained in the sample rack;

a transfer line for transferring a sample rack supplied from said rack supply unit to the analyzing unit and for transferring the sample rack from the analyzing unit to an exit of the transfer line;

a standby unit for keeping sample racks having a probability of being reexamined in a standby state;

a returning line for returning the sample rack to an entrance side of said transfer line after sampling;

a rack collecting unit for housing sample racks not required to be reexamined;

a directing device for selectively directing a sample rack from said transfer line to a selected one of said standby unit and said rack collecting unit based on whether a sample on said sample rack has a probability of requiring reexamination;

wherein a path from said transfer line to said rack collecting unit and a path from said standby unit to said returning line cross at a cross position, said standby unit being provided with an entrance adjacent to said transfer line and an exit adjacent to said cross position; and a control unit for controlling said directing device so that a sample rack preregistered as a sample rack not required to be reexamined is moved from said directing device to said rack collecting unit through said cross position without first passing through the returning line, and so that a sample rack having a probability of being reexamined is moved from said directing device into said standby unit without first passing through said returning line.

2. An automatic analyzing apparatus according to claim 1, wherein said control unit controls said directing device so that when a leading sample rack in said standby unit is judged not to need reexamination on the basis of a result of examination in said analyzing unit, said leading sample rack is moved to said rack collecting unit after being positioned at said cross position, and when said leading sample rack is judged to need reexamination on the basis of a result of examination in said analyzing unit, said leading sample rack is moved to said returning line through said cross position.

3. An automatic analyzing apparatus according to claim 1, wherein a sample rack that does not need to be reexamined is any one of a control sample rack, a reference sample rack and a cleaning solution rack.

4. An automatic analyzing apparatus according to claim 1, wherein a position of directing sample racks by said directing device and an entrance of said rack collecting unit are arranged on an extending line of said transfer line.

5. An automatic analyzing apparatus according to claim 1, wherein a position of directing sample racks by said directing device also serves as an entrance of said standby unit.

6. An automatic analyzing apparatus, comprising:

a rack supplying unit capable of containing sample racks;

an analyzing unit for testing an analysis item of a sample sampled from a sample container contained in the sample rack;

a transfer line for transferring a sample rack supplied from said rack supply unit to a position corresponding to the analyzing unit, and for transferring the sample rack after being sampled to an exit of the transfer line;

a standby unit for keeping sample racks having a probability of being reexamined in a standby state;

a returning line for returning the sample rack to an entrance side of said transfer line after sampling; and a rack collecting unit for housing sample racks not required to be reexamined;

wherein a transfer passage from the exit of said transfer line to said rack collecting unit and a passage for moving a sample rack at said standby unit to an entrance of said returning line are arranged so as to cross to each other.

7. An automatic analyzing apparatus according to claim 6, wherein a sample rack at said standby unit is directed so as to be transferred to a selected one of the entrance of said returning line and said rack collecting unit by a directing apparatus in response to an examination result of said analyzing unit.

8. An automatic analyzing apparatus according to claim 1, wherein a sample rack standing-by at said standby unit is transferred from the exit of said transfer line to said rack collecting unit during a stop motion period of a transferring operation of transferring sample racks to the entrance of said returning line.

9. An automatic analyzing apparatus according to claim 1, wherein said standby unit comprises a receiving area for receiving a sample rack from the entrance of said standby unit, and a sending-out area for sending out a received sample rack to the exit of said standby unit after a standby time, and wherein both of said receiving area and said sending-out area form a U-shaped transferring passage.

10. An automatic analyzing apparatus according to claim 9, wherein a conveyer belt is provided in said sending-out area, and wherein said conveyer belt performs transferring of a sample rack inside said standby unit and transferring of a sample rack from the exit of said standby unit to the entrance of said returning line.

11. An automatic analyzing apparatus according to claim 10, wherein said conveyer belt comprises a plurality of partitioning members for partitioning between sample racks in the sending-out area, and wherein said partitioning members are positioned so as to pass a sample rack from the exit of said transfer line to said rack collecting unit while said conveyer belt is stopped to be operated.

* * * * *